US011363996B2

(12) United States Patent
Chen et al.

(10) Patent No.: US 11,363,996 B2
(45) Date of Patent: Jun. 21, 2022

(54) EARLY WARNING METHOD, DEVICE AND SYSTEM OF SUDDEN DEATH

(71) Applicant: XI'AN JIAOTONG UNIVERSITY, Xi'an (CN)

(72) Inventors: Xiang Chen, Xi'an (CN); Jin Li, Xi'an (CN); Zhongbo Bai, Xi'an (CN); Xu Zhang, Xi'an (CN); Huakui Yang, Xi'an (CN); Peiyuan Huang, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 0 days.

(21) Appl. No.: 16/967,422

(22) PCT Filed: Dec. 26, 2018

(86) PCT No.: PCT/CN2018/124055
§ 371 (c)(1),
(2) Date: Aug. 5, 2020

(87) PCT Pub. No.: WO2019/153929
PCT Pub. Date: Aug. 15, 2019

(65) Prior Publication Data
US 2021/0212639 A1 Jul. 15, 2021

(30) Foreign Application Priority Data
Feb. 11, 2018 (CN) .......................... 201810142202.8

(51) Int. Cl.
A61B 5/0205 (2006.01)
A61B 5/00 (2006.01)
(Continued)

(52) U.S. Cl.
CPC ............ A61B 5/746 (2013.01); A61B 5/0022 (2013.01); A61B 5/0205 (2013.01);
(Continued)

(58) Field of Classification Search
CPC . A61B 5/0022; A61B 5/0205; A61B 5/02405; A61B 5/02416; A61B 5/0245;
(Continued)

(56) References Cited

U.S. PATENT DOCUMENTS

2008/0058615 A1 3/2008 Clapp
2016/0324442 A1* 11/2016 Zdeblick ................ A61B 5/073
(Continued)

FOREIGN PATENT DOCUMENTS

| CN | 201814561 U | 5/2011 |
| CN | 103932688 A | 7/2014 |
| CN | 107126203 A | 9/2017 |
| CN | 108309261 A | 7/2018 |

OTHER PUBLICATIONS

Karlen et al. Improving the Accuracy and Efficiency of Respiratory Rate Measurements in Children Using Mobile Devices, Jun. 2014 (Year: 2014).*

(Continued)

Primary Examiner — Benyam Haile
(74) Attorney, Agent, or Firm — W&G Law Group

(57) ABSTRACT

The present application discloses an early warning method, device and system of sudden death. The method includes: 1. extracting 6 indicators of 4 types of physiological information 2. performing abnormality detection on the physiological information and calculating an early warning level, proceeding to step 3 when a result of the abnormality detection indicates abnormal, and continuing the abnormality detection when the result of the abnormality detection indicates normal; and 3. producing sound, light and vibration alarms, in which an alarm device is driven to produce sound, light and vibration and provide a corresponding early warning level. A higher early warning level indicates a higher risk of sudden death.

4 Claims, 3 Drawing Sheets

(51) Int. Cl.
    *G08B 7/06*     (2006.01)
    *A61B 5/024*     (2006.01)
    *A61B 5/0245*     (2006.01)
    *A61B 5/08*     (2006.01)
    *A61B 5/1455*     (2006.01)

(52) U.S. Cl.
    CPC ............ *A61B 5/7275* (2013.01); *A61B 5/742* (2013.01); *A61B 5/7405* (2013.01); *A61B 5/7455* (2013.01); *G08B 7/06* (2013.01); *A61B 5/0245* (2013.01); *A61B 5/02405* (2013.01); *A61B 5/02416* (2013.01); *A61B 5/0816* (2013.01); *A61B 5/14551* (2013.01)

(58) Field of Classification Search
    CPC ..... A61B 5/0816; A61B 5/746; A61B 5/7275; A61B 5/7405; A61B 5/742; A61B 5/7455; A61B 5/14551; G08B 7/06
    See application file for complete search history.

(56) References Cited

U.S. PATENT DOCUMENTS

| | | | |
|---|---|---|---|
| 2017/0027527 A1* | 2/2017 | Bhat | A61N 1/36585 |
| 2017/0055898 A1* | 3/2017 | Bandyopadhyay | A61B 5/11 |
| 2018/0049652 A1* | 2/2018 | Al Ahmad | A61B 5/7282 |
| 2018/0085040 A1* | 3/2018 | Ferber | A61B 5/746 |
| 2020/0054583 A1* | 2/2020 | Wellman | A61K 31/222 |

OTHER PUBLICATIONS

Karmakar et al—Analyzing temporal variability of standard descriptors of Poincaré plots, May 2010 (Year: 2010).*
International Search Report (PCT/CN2018/124055); dated Mar. 28, 2019.

* cited by examiner

EARLY WARNING METHOD, DEVICE AND SYSTEM OF SUDDEN DEATH

CROSS-REFERENCE TO RELATED APPLICATIONS

This is the United States national phase of International Patent Application No. PCT/CN2018/124055, filed on Dec. 26, 2018, which claims priority of Chinese patent application No. 2018101422028, filed on Feb. 11, 2018, the entire contents of which are incorporated herein by their references.

TECHNICAL FIELD

The present application relates to the field of biomedical engineering, and specifically, to an early warning method, an early warning device, and an early warning system of sudden death.

BACKGROUND

Sudden death is defined by the World Health Organization as "patients who are generally healthy or seemingly healthy die suddenly due to natural diseases in an unexpectedly short period of time". According to a report of the World Health Organization, ischemic heart disease, stroke and hypertensive heart disease among the top ten causes of death worldwide are directly related to sudden death. 15.2 million deaths were caused by these three causes worldwide from 2000 to 2012, accounting for more than 25% of total deaths. The sudden deaths have increased year by year, and are widely distributed in low- to middle-income countries, upper-middle income countries, and high-income countries. The sudden death, which is characterized by a large number of deaths, a high morbidity rate, an increase in deaths year by year, and a wide distribution of morbidity crowd, is a serious disease worldwide. Every year, 1.8 million domestic people die from sudden death, with an average of 3 to 4 sudden deaths per minute.

The majority of sudden deaths are caused by cardiac arrest. 40% of cardiac arrests are not found or occur during sleep; 70% to 80% of cardiac arrests occur at home; and 72% to 80% of the deaths caused by cardiac arrest occurs outside the hospital or at home. In view of the causes and classifications, 80-90% of sudden death events are caused by diseases of the cardiovascular system, respiratory system and nervous system, and only 10-20% are caused by diseases of the digestive system, urogenital system and other diseases. According to the existing sudden death prevention system, a primary prevention and a secondary prevention are adopted to protect people having these diseases and high-risk groups, in order to improve a survival rate after onset. However, nearly ⅓ of sudden deaths have no obvious signs of cardiovascular disease in advance, it is difficult for the existing public health prevention system to provide effective precaution for all people.

China patent CN 103932688A discloses an early warning device of sudden death and a watch using the early warning device, in which the pulse information detected through a green LED in combination with human motion information obtained by a three-axis acceleration sensor are used to provide early warning of a sudden death and reflect abnormalities caused by diseases of the cardiovascular system to a certain extent. China patent CN 104688250A discloses an early warning method and an early warning system for assessing mental stress and sudden cardiac death, in which an integrated electromyographic sensor and a heart rate sensor are used to obtain abnormal electromyographic signals caused by mental stress, and abnormal signals in heart rate deceleration force and continuous heart rate deceleration force caused by abnormal heart rate, which reflect the abnormalities caused by mental and cardiovascular diseases.

In the existing early warning methods and early warning devices of sudden death represented by the above methods, the abnormalities caused by cardiovascular system diseases are monitored and early warned usually by using photoelectric volume pulse waves as the main detection pulse or heart rate signal supplemented with the monitoring of the motion information and the electromyographic abnormality caused by mental stress. In this regard, the monitoring indicators are less diverse, and it is difficult to monitor and warn abnormalities caused by diseases of the respiratory system, nervous system and other systems. A missed alarming rate and a false alarm rate are relatively high, which are insufficient to provide monitoring and early warning for the majority of sudden death factors and for the entire population.

SUMMARY

In view of the problems in the prior art, the present application provides an early warning method, an early warning device, and an early warning system of sudden death. In the present application, the diseases of the cardiovascular system, nervous system, and respiratory system, which are the main causes of 80 to 90% of sudden deaths, are prevented and monitored by monitoring four physiological signals in a multi-source information fusion manner. The apparatus is simple in structure, easy to be implemented, small in size, and consumes less power.

The present application includes the following technical solutions.

An early warning method of sudden death including the following steps:

Step 1: extracting and detecting physiological information, wherein information about respiration, blood oxygen saturation, heart rate and heart rate variability of a subject is extracted and detected to obtain six monitoring indicators comprising a respiratory rate, an AHI index, an arterial oxygen saturation, a heart rate, and Poincaré map indicators SD1 and SD2;

Step 2: performing abnormality detection on the physiological information and calculating an early warning level, proceeding to step 3 when a result of the abnormality detection indicates abnormal, and continuing the abnormality detection when the result of the abnormality detection indicates normal, wherein an abnormality detection is performed on the physiological information obtained in Step 1, wherein when calculating the early warning level, an initial early warning level is 0, the early warning level is incremented by 1 for every occurrence of an abnormality of any one indicator of the respiratory rate, the arterial oxygen saturation, the heart rate, the SD1, and the SD2, and the early warning level is incremented by 1 when the AHI index is slightly abnormal, by 2 when the AHI index is moderately abnormal, or by 3 when the AHI index is severely abnormal; and Step 3: producing sound, light and vibration alarms, wherein an alarm device is driven to produce at least one of the sound, light and vibration alarms to remind a user or a guardian of the user, and provide a corresponding early warning level, wherein a higher early warning level indicates a higher risk of sudden death, the early warning level greater than 3 indicates a necessity of medical attention, and the early warning level greater than 5 indicates a necessity of emergency medical attention.

Preferably, the early warning method of sudden death further includes the following steps subsequent to Step 3:

Step 4: generating an alarming log or a monitoring log, wherein when the result of the abnormality detection in Step 2 indicates normal, the monitoring log is generated, or When the result of the abnormality detection in Step 2 indicates abnormal, the alarming log is recorded and generated after the alarms are produced in Step 3;

Step 5: transmitting data through network, wherein the obtained original physiological signals, the generated alarming log, and the generated monitoring log are transmitted to a network server terminal for data analysis processing and storage backup; and Step 6: feeding back expert diagnosis and treatment information, wherein abnormal data obtained by monitoring are pushed by the network server to a medical care terminal, where a medical expert makes an early waning assessment on a risk of sudden death, and formulates and feeds back corresponding diagnosis and treatment guidance to the user or the guardian of the user through network.

Preferably, the information about respiration reflects a working status of a respiratory system, and the respiratory rate and an apnea hypopnea index AHI during sleep are monitored respectively;

the detecting of the respiratory rate is described with an equation (1):

$$RESP = \frac{60}{T_{RESP}} \quad (1)$$

where $T_{RESP}$ denotes a respiratory interval in a detected respiratory wave; and the apnea hypopnea index AHI denotes a number of times of apnea plus hypopnea per hour of sleep.

Preferably, the information about arterial blood oxygen saturation reflects both a working status of a respiratory system and a working status of a cardiovascular system;

the arterial oxygen saturation is detected by a dual-wavelength photoplethysmographic (PPG) sensor with red light at a wavelength of 660 nm and infrared light at a wavelength of 940 nm, and is described with equations (2) and (4), or (3) and (4):

$$S_pO_2 = \alpha - \beta R; \quad (2)$$

$$S_pO_2 = \alpha - \beta R - \gamma R^2; \quad (3)$$

$$R = \frac{I_{AC}^{660}/I_{DC}^{660}}{I_{AC}^{940}/I_{DC}^{940}}, \quad (4)$$

where $I_{AC}^{660}$ and $I_{AC}^{940}$ denote respectively an AC component of an intensity of the red light and an AC component of an intensity of the infrared light, $I_{DC}^{660}$ and $I_{DC}^{940}$ denote respectively a DC component of the intensity of the red light and a DC component of the intensity of the infrared light, and $\alpha$, $\beta$ and $\gamma$ each denote an empirical value; and the equation (2) denotes a first-order linear relation between the blood oxygen saturation and a R value, and the second-order equation (3) is used when the first-order relation is not linear.

Preferably, the information about heart rate reflects a working status of a cardiovascular system, and the heart rate is detected and described with an equation (5):

$$HR = \frac{60}{T_{RR}}, \quad (5)$$

where $T_{RR}$ denotes a heart rate interval in a body surface electrocardiogram or a photoplethysmographic (PPG).

Preferably, the Poincaré map indicators SD1 and SD2 reflect both a working status of a cardiovascular system and a working status of a nervous system;

the heart rate variability is extracted and detected by a non-linear analysis method of heart rate variability, and the standard deviations SD1 and SD2 of Poincaré map in a heart rate interval are calculated, as described in equations (6) and (7):

$$SD1^2 = \frac{1}{N-1}\sum_{i=1}^{N-1}(D_i')^2, \quad (6)$$

$$SD2^2 = \frac{1}{N-1}\sum_{i=1}^{N-1}(D_i'')^2, \quad (7)$$

where $D'_i$ and $D''_i$ are described in equations (8) and (9), and N denotes a total number of heart rate intervals:

$$D_i' = \frac{1}{\sqrt{2}}|TRR_n - TRR_{n+1}|, \quad (8)$$

$$D_i' = \frac{1}{\sqrt{2}}|TRR_n + TRR_{n+1} - 2\overline{TRR}|, \quad (9)$$

where $TRR_n$ and $TRR_{n+1}$ denote respectively an $n^{th}$ heart rate and a $(n+1)^{th}$ heart rate interval, $\overline{TRR}$ denotes an interval mean value of all heart rate intervals, and n is a natural number.

Preferably, in Step 2, a normal respiratory rate ranges from 10 times/min to 24 times/min, and an respiratory rate greater than 24 times/min or smaller than 10 times/min is abnormal; AHI smaller than or equal to 5 is normal, AHI greater than 5 and smaller than or equal to 15 is slightly abnormal, AHI greater than 15 and smaller than or equal to 30 is moderately abnormal, and AHI greater than 30 is severely abnormal; the arterial oxygen saturation greater than or equal to 90% is normal, and the arterial oxygen saturation smaller than 90% is abnormal; the heart rate in a range of 60 times/min to 100 times/min is normal, and the heart rate greater than 100 times/min or smaller than 60 times/min is abnormal; and the Poincaré map indicators SD1 and SD2 are normal when an empirical value of SD1 is greater than or equal to 10 ms and an empirical value of SD2 is greater than or equal to 20 ms, and the Poincaré map indicators SD1 and SD2 are abnormal when an empirical value of SD1 is smaller than 10 ms or an empirical value of SD2 is smaller than 20 ms.

An early warning device of sudden death includes: a respiratory sensor module configured to extract and detect information about respiration of a user; a blood oxygen saturation sensor module configured to extract and detect information about blood oxygen saturation of the user; a heart rate sensor module configured to extract and detect information about heart rate and information about heart rate variability of the user; and a microprocessor module configured to perform an abnormality detection and calculate an early warning level. The microprocessor module receives physiological signals transmitted from the respiratory sensor module, the blood oxygen saturation sensor module and the heart rate sensor module, and outputs alarm information and original data to an alarming module, a data transmission module and a data storage module. The alarming module is configured to produce sound, light and vibration alarms based on outputs of the microprocessor module, and the data transmission module is configured to transmit the original data and the data storage module is configured to store the original data.

Preferably, the microprocessor module includes an MSP430 single chip computer; and the data storage module includes a Micro-SD card module or a FLASH module.

An early warning system of sudden death includes: the early warning device of sudden death as described above and configured to collect respective physiological signals, determine whether the respective physiological signals are abnormal or not, and alarm abnormal information; a mobile terminal or computer configured to transmit the physiological information collected by the early warning device of sudden death, as well as the alarming log or the monitoring log to a network server; a network server configured to perform large data analysis, processing, storage and backup of the physiological information and the alarming log or the monitoring log that are transmitted from the mobile terminal or computer; and a medical care terminal connected to the network server and configured to analyze and process the uploaded physiological information and the alarming log or the monitoring log by a doctor, and formulate and feed back a diagnosis and treatment guidance to the user or a guardian of the user for execution. The early warning device of sudden death is in wired or wireless data communication with the mobile terminal or computer.

Compared with the prior art, the present application brings the following beneficial effects.

In the present application, instead of the technology that only monitors the information about heart rate of the cardiovascular system in the prior art, the early warning levels are constructed using the six monitoring indicators of the four kinds of physiological information in a multi-source information fusion manner, so as to simultaneously monitor the information about respiratory RESP, blood oxygen saturation SpO2, heart rate HR, and heart rate variability HRV that may characterize a state of autonomic nerve activities, highly related to functions of the cardiovascular system, respiratory system and nervous system. By monitoring these four physiological signals, the diseases of the cardiovascular system, nervous system, and respiratory system, which are the main causes of 80 to 90% of sudden deaths, are prevented and monitored. In this way, a monitoring scope is expanded, and the missed warning rate is reduced, solving the problems that nearly ⅓ of sudden deaths have no obvious signs of cardiovascular disease in advance. By specifically classifying the early warning levels, the current problem of a high false warning rate can be solved. A warning network system can be easily built through the internet to expand the protection scope of early warning of sudden death, thereby satisfying the requirements of different application scenarios such as families, communities, large and medium-sized medical institutions.

DESCRIPTION OF EMBODIMENTS

The present application will be further described in detail below in conjunction with specific embodiments, which are intended to explain the present application, rather than limiting the present application.

The present application provides an early warning method, an early warning device, and an early warning system of sudden death, overcoming the deficiencies of the exiting sudden death early-warning methods, such as less diversity of the monitoring indicators, difficulties in monitoring and early warning of abnormalities caused by diseases of respiratory system, nervous system and other systems, high missed warning rate and high false warning rate, and insufficiencies in providing monitoring and early warning for the majority of sudden death factors and for the entire population.

In the present application, instead of the technology that only monitors the information about heart rate of the cardiovascular system, information about respiratory RESP, blood oxygen saturation SpO2, heart rate HR, and heart rate variability HRV that may characterize a state of autonomic nerve activities, highly related to functions of the cardiovascular system, respiratory system and nervous system, are simultaneously monitored. The diseases of the cardiovascular system, nervous system, and respiratory system, which are the main causes of 80 to 90% of sudden deaths, are prevented and monitored by monitoring these four types of physiological signals in a multi-source information fusion manner. In this way, a monitoring scope is expanded, and the missed warning rate is reduced, solving the problems that nearly ⅓ of sudden deaths have no obvious signs of cardiovascular disease in advance. Six monitoring indicators of these four physiological signals are used to construct warning levels in the multi-source information fusion manner. The early warning level is incremented by 1 for every occurrence of an abnormality of any one indicator of the respiratory rate, the arterial oxygen saturation, the heart rate, SD1, and SD2; and the early warning level is incremented by 1 as the severity of the AHI index is incremented by one order. A higher warning level indicates a higher risk of sudden death of the user, the early warning level greater than 3 indicates a necessity of medical attention, and the early warning level greater than 5 indicates a necessity of emergency medical attention. In this way, the current situation of the prior art lacking early warning level classification and having a high false warning rate is changed.

Figure 1:
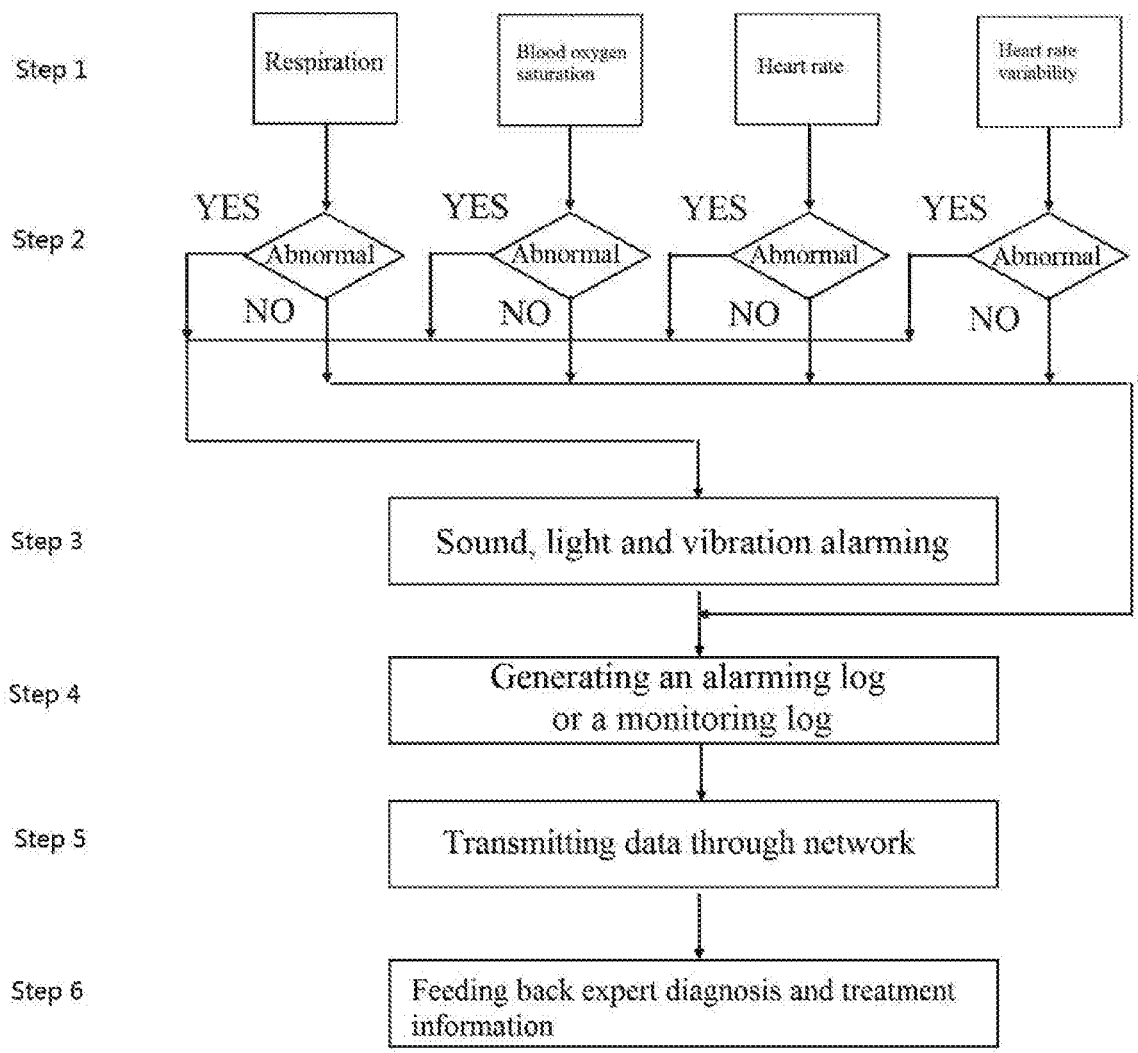
FIG. 1 is a flow diagram of an early warning method of sudden death according to the present application.

As shown in FIG. 1, the early warning method of sudden death of the present application includes the following steps:

Step 1: extracting and detecting physiological information. Information about respiration, information about blood oxygen saturation, information about heart rate, and information about heart rate variability of a subject are respectively extracted and detected with one or more sensors. The information about respiration mainly indicates a working status of the respiratory system, and the respiratory rate and an apnea hypopnea index (AHI) are monitored, respectively. The information about arterial blood oxygen saturation indicates both a working status of the respiratory system and a working status of the cardiovascular system. The information about heart rate indicates a working status of the cardiovascular system. The Poincaré map indicators SD1, SD2, which are obtained through a nonlinear analysis of the heart rate variability, indicate both a working status of the cardiovascular system and a working status of the nervous system. By monitoring the above physiological parameters, the user can easily and conveniently learn about the working statuses of the cardiovascular system, respiratory system and nervous system. The information about respiration, the information about blood oxygen saturation, the information about heart rate, and the information about heart rate variability are detected in parallel without any priority relationship during execution.

Step 2: performing an abnormality detection on the physiological information. An abnormality detection is performed on the physiological information obtained in Step 1 and an early warning level is calculated.

Step 3: producing sound, light and vibration alarms. If the result of the abnormality detection of the physiological information obtained in Step 2 indicates abnormal, an alarm device is driven to produce at least one of the sound, light and vibration alarms to remind the user or a guardian of the user to pay close attention to the user's physical conditions, and to take an appropriate medical treatment or a first aid measure according to the prompted early-warning level. If the detection result indicates normal, Step 3 is skipped and Step 4 is executed.

Step 4: generating an alarming log or a monitoring log. According to the result of the abnormality detection of the physiological information obtained in Step 2, an alarm log or a monitoring log is established. If the result indicates abnormal, the alarming log is recorded, and if the result indicates normal, the monitoring log is recorded.

Step 5: transmitting data through network. The obtained original physiological signals and the generated alarming and monitoring logs are transmitted to a network server terminal through internet for subsequent data analysis processing and storage backup.

Step 6: feeding back expert diagnosis and treatment information. The abnormal data obtained by monitoring are pushed by the network server to a medical care terminal, where a medical expert makes an early waning assessment on a risk of sudden death, and formulates and feeds back corresponding diagnosis and treatment guidance to the user or the guardian of the user through network.

Preferably, in Step 1, the detection of the respiratory rate is described with equation (1):

$$RESP = \frac{60}{T_{RESP}}, \quad (1)$$

where $T_{RESP}$ denotes a respiratory interval in a detected respiratory wave, in a unit of second.

Preferably, in Step 1, the apnea hypopnea index (AHI) refers to a number of times of apnea plus hypopnea per hour of sleep. The apnea means that a breathing airflow through the mouth and nose completely stops for 10 seconds or more during sleep, and the hypopnea means that an intensity of the breathing airflow is reduced during sleep by 50% or more from a basic level, accompanied by a decrease of more than 4% in blood oxygen saturation from the basic level or microarousal.

Preferably, in Step 1, the arterial blood oxygen saturation is detected by a dual-wavelength photoplethysmographic (PPG) sensor with red light at 660 nm and infrared light at 940 nm, and is described with equations (2) and (4), or (3) and (4):

$$S_P O_2 = \alpha - \beta R \quad (2)$$

$$S_P O_2 = \alpha - \beta R - \gamma R^2 \quad (3)$$

$$R = \frac{I_{AC}^{660}/I_{DC}^{660}}{I_{AC}^{940}/I_{DC}^{940}}. \quad (4)$$

In the equations, $I_{AC}^{660}$ and $I_{AC}^{940}$ denote respectively an AC component of an intensity of the red light and an AC component of an intensity of the infrared light, and $I_{DC}^{660}$ and $I_{DC}^{940}$ denote respectively a DC component of the intensity of the red light and a DC component of the intensity of the infrared light. Accordingly, when the DC and AC components of the intensities of the red light and the infrared light are obtained during a heartbeat cycle, the R value can be calculated, and then the blood oxygen saturation within the heartbeat cycle can be calculated.

$\alpha$, $\beta$ and $\gamma$ each denotes an empirical value, which is determined by calibration. The equation (2) is a first-order linear relation between the blood oxygen saturation and the R value, which is described with the second-order equation (3) when the first-order relation is not linear.

Preferably, in Step 1, the detection of the heart rate is described with an equation (5):

$$HR = \frac{60}{T_{RR}} \quad (5)$$

where $T_{RR}$ denotes a heart rate interval in a body surface electrocardiogram or photoplethysmographic (PPG), in a unit of second.

Preferably, in Step 1, the heart rate variability is extracted and detected by a non-linear analysis method of heart rate variability, and standard deviations SD1, SD2 of the Poincaré map in a heart rate interval are calculated, as described in equations (6) and (7):

$$SD1^2 = \frac{1}{N-1} \sum_{i=1}^{N-1} (D'_i)^2 \quad (6)$$

$$SD2^2 = \frac{1}{N-1} \sum_{i=1}^{N-1} (D''_i)^2 \quad (7)$$

where $D'_i$ and $D''_i$ are as described in equations (8) and (9), and N denotes a total number of the heart rate intervals:

$$D'_i = \frac{1}{\sqrt{2}} |TRR_n - TRR_{n+1}| \quad (8)$$

$$D'_i = \frac{1}{\sqrt{2}} |TRR_n + TRR_{n+1} - 2\overline{TRR}| \quad (9)$$

where $TRR_n$ and $TRR_{n+1}$ denote respectively an $n^{th}$ heart rate interval and a $(n+1)^{th}$ heart rate interval, $\overline{TRR}$ denotes an interval mean value of all heart rate intervals, and n is an natural number.

Preferably, in Step 2, in practically clinical applications, a normal respiratory rate of an adult ranges from 10 times/min to 24 times/min. The respiratory rate greater than more than 24 times/min is called shallow breathing, and the respiratory rate smaller than 10 times/min is called slowed respiratory rate, which are both abnormal.

Preferably, in Step 2, in practically clinical applications, AHI smaller than or equal to 5 is normal, greater than 5 and smaller than or equal to 15 is slightly abnormal, AHI greater than 15 and smaller than or equal to 30 is moderately abnormal, and AHI greater than 30 is severely abnormal.

Preferably, in Step 2, in practically clinical applications, the arterial oxygen saturation greater than or equal to 90% is normal, and the arterial oxygen saturation smaller than 90% (referred as to hypoxemia) is abnormal.

Preferably, in Step 2, in practically clinical applications, a normal value of the heart rate when a normal adult is in a resting state ranges from 60 times/min to 100 times/min. The heart rate greater than 100 times/min is called sinus tachycardia, and the heart rate smaller than 60 times/min is called sinus bradycardia, which are both abnormal.

Preferably, in Step 2, in practically clinical applications, no standards are available for evaluating the Poincaré map indicators SD1 and SD2 obtained through a non-linear analysis method of the heart rate variability of a normal adult. Currently, the empirical value of SIM greater than or equal to 10 ms and the empirical value of SD2 greater than or equal to 20 ms are considered as normal, while the empirical value of SD1 smaller than 10 ms or the empirical value of SD2 smaller than 20 ms is considered as abnormal.

Figure 4A:
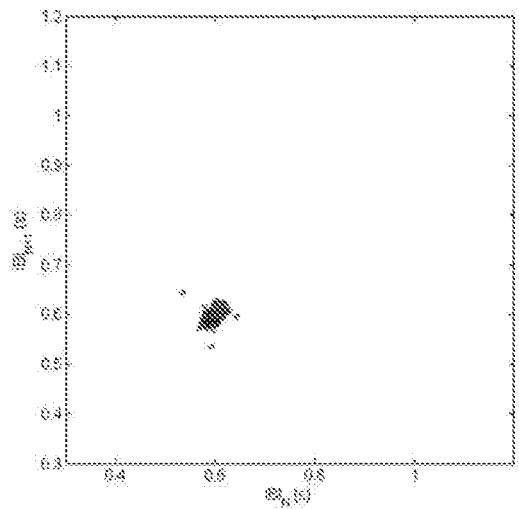
FIG. 4a is a Poincaré map of an analysis of heart rate variability before a sudden death.
Figure 4B:
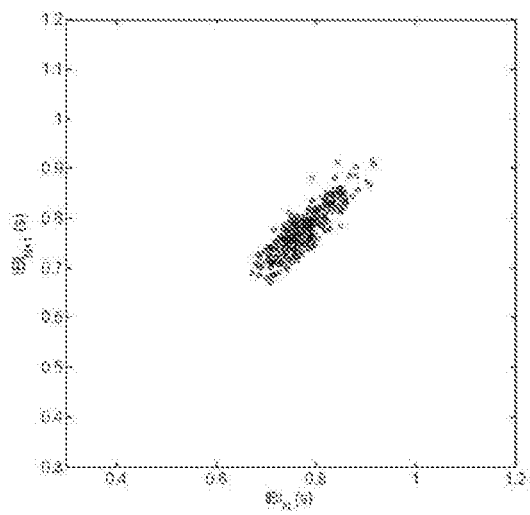
FIG. 4b is a Poincaré map of an analysis of heart rate variability of a healthy person.

FIG. 4a and FIG. 4b provide a comparison between the Poincaré map of an analysis of the heart rate variability before sudden death and an analysis of the heart rate variability of healthy people. FIG. 4a is a Poincaré map of an analysis of heart rate variability before a sudden death, in which SD1 is 7.8 ms and SD2 is 12.4 ms; and FIG. 4b is a Poincaré map of an analysis of heart rate variability of healthy people, in which SD1 is 17.5 ms and SD2 is 64.4 ms, a significant difference in graphic distribution between the two figures can be observed.

Preferably, in Step 2, the early warning level is specifically calculated as below:

Among the above mentioned six monitoring indicators, the respiratory rate, the AHI index, the arterial oxygen saturation, the heart rate, and the Poincaré map indicators SD1 and SD2 obtained by the non-linear analysis method of the heart rate variability, the early warning level is incremented by 1 for every occurrence of an abnormality of any one indicator of the respiratory rate, the arterial oxygen saturation, the heart rate, SD1, and SD2, and the early warning level is incremented by 1 when the AHI index is slightly abnormal, by 2 when the AHI index is moderately abnormal, or by 3 when the AHI index is severely abnormal. A higher early warning level indicates a higher risk of sudden death, the early warning level greater than 3 indicates a necessity of medical attention, and the early warning level greater than 5 indicates a necessity of emergency medical attention.

Figure 2:
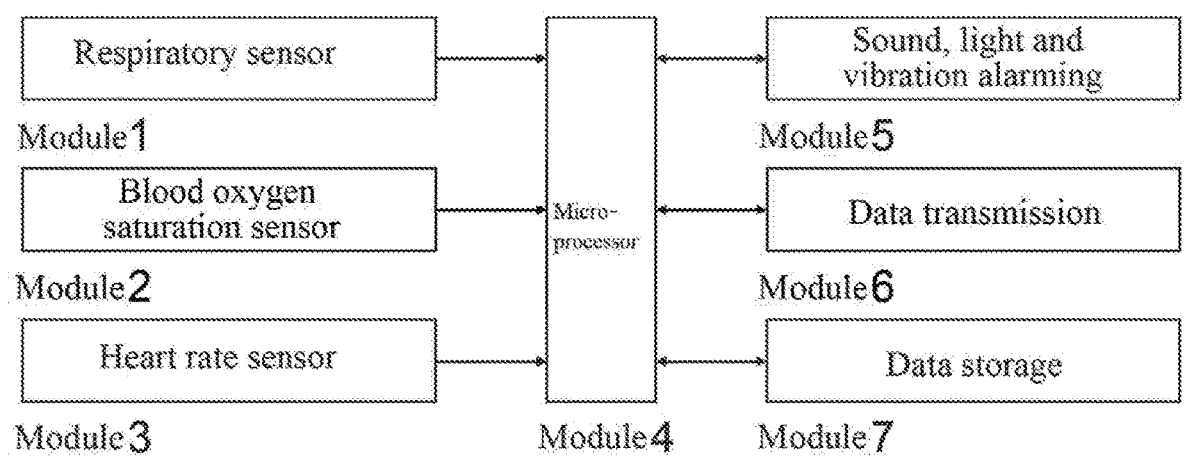
FIG. 2 is a structural schematic diagram of an early warning device of sudden death according to the present application.

Correspondingly, FIG. 2 illustrates an early warning device of sudden death, including the following modules 1 to 7.

The module 1 is a respiratory sensor module, which is a respiratory bandage, an oral and nasal airflow sensor, an ECG transthoracic impedance sensor, a photoplethysmographic (PPG) sensor, or other respiratory rate sensors. The oral and nasal airflow sensor that can provide information about oral and nasal airflow, or the low-cost photoplethysmographic (PPG) sensor is preferable. This module is configured to extract and detect information about respiration of the user.

The module 2 is a blood oxygen saturation sensor module. It may be a photoelectric sensor capable of detecting blood oxygen saturation at body parts including fingertip capillary bed, wrist radial artery, and earlobe capillary bed, etc. It may be transmissive or reflective. A content of oxyhemoglobin in hemoglobin is obtained through biological tissue absorbing and attenuating the red light at a wavelength of 660 nm and the infrared light at a wavelength of 940 nm, so as to detect the oxygen content in the blood. Preferable is a dual-wavelength reflective photoelectric volume sensor that is not restricted by the body part using the sensor.

The module 3 is a heart rate sensor module. It may be a single lead ECG a transmissive or reflective single/dual wavelength photoelectric pulse heart rate meter, or a pulse oximeter that can obtain the information about heart rate. This module is configured to extract and detect the information about heart rate variability that reflects a status of the autonomic nerve. Preferable is a reflective dual-wavelength photoplethysmographic (PPG) sensor having a sampling rate of 500 S/s or greater.

The module 4 is a microprocessor module. It may be a central processor or a controller configured to control the operation of the early warning device. Preferable is a low-power consumption single chip computer of MSP430 series, manufactured by Texas Instruments.

The module 5 is a sound, light, and vibration alarming module. The sound, light and vibration alarming module is composed of a micro speaker, a LED alarm light and a vibration motor. The frequency of the sound, light and vibration alarming is determined by the early warning level. The higher early warning level indicates the higher risk faced by the user, and corresponds to a higher alarming frequency. Preferably, a mobile terminal such as mobile phone and tablet computer is employed.

The module 6 is a data transmission module. The original data obtained by each sensor is transmitted to a mobile terminal such as mobile phone and tablet computer or a personal computer in a wireless manner, for example, through Bluetooth or WIFI, or through wires. Then, the original data are transmitted to the network server through network. Preferably, a mobile terminal such as mobile phone and tablet computer is employed.

The module 7 is a data storage module. The data storage module may be, for example, a Micro-SD card module, or a FLASH module, for storing and recording the original data obtained by each sensor. The stored data can be uploaded to the network server terminal as needed. Preferably, a mobile terminal such as mobile phone and tablet computer is employed.

Figure 3:
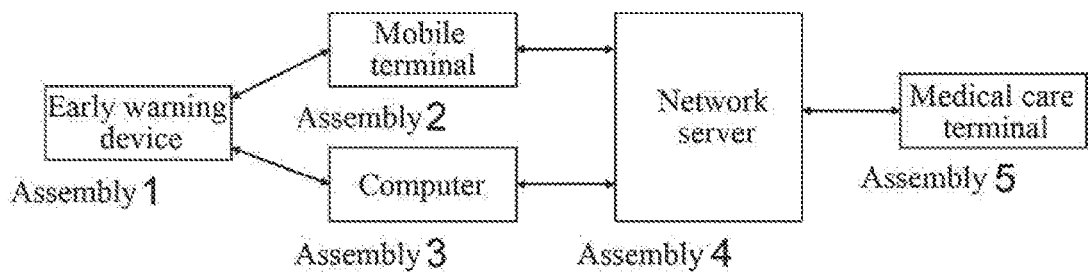
FIG. 3 is a network structure diagram of an early warning system of sudden death according to the present application.

Correspondingly, FIG. 3 illustrates an early warning system of sudden death, including the following assemblies 1 to 5.

The assembly 1 is an early warning device, i.e., the early warning device of sudden death according to the present application, for collecting the respective physiological signals, determining whether the respective physiological signals are abnormal or not, and alarming the abnormal information. The early warning device of sudden death may be in wired or wireless data communication with a mobile terminal of the assembly 2 or a personal computer of the assembly 3.

The assembly 2 is a mobile terminal. It can be a smart phone or a tablet computer for transmitting the physiological information collected by the early warning device of sudden death, as well as the alarming and monitoring logs to a network server of the assembly 4.

The assembly 3 is a computer. It may be a personal computer or a tablet computer, etc., for transmitting the physiological information collected by the early warning device of sudden death, as well as the alarming and monitoring logs to the network server of the assembly 4.

The assembly 4 is a network server configured to performing large data analysis, storage and backup of the physiological information as well as the alarming and monitoring logs that are transmitted from the mobile terminal of the assembly 2 or the computer of the assembly 3.

The assembly 5 is a medical care terminal. The medical care terminal is connected to the network server, and configured to analyze and process the uploaded physiological information, the alarming log and the monitoring log by a doctor and formulate and feed back a diagnosis and treatment guidance to the user or the guardian of the user for execution, The formed early warning system network includes a large number of early warning devices, mobile terminals, computers, medical care terminals and multiple network servers, which can ensure the timely and accurate processing and early warning of various abnormal physiological signals from all users during operation.

What is claimed is:

1. An early warning method of sudden death, comprising:
Step 1: extracting and detecting physiological information, wherein information about respiration, blood oxygen saturation, heart rate and heart rate variability of a subject is extracted and detected to obtain six monitoring indicators comprising a respiratory rate, an AHI index, an arterial oxygen saturation, a heart rate, and Poincaré map indicators SD1 and SD2;
Step 2: performing abnormality detection on the physiological information and calculating an early warning level, proceeding to step 3 when a result of the abnormality detection indicates abnormal, and continuing the abnormality detection when the result of the abnormality detection indicates normal, wherein an abnormality detection is performed on the physiological information obtained in Step 1, wherein when calculating the early warning level, an initial early warning level is 0, the early warning level is incremented by 1 for every occurrence of an abnormality of any one indicator of the respiratory rate, the arterial oxygen saturation, the heart rate, the SD1, and the SD2, and the early warning level is incremented by 1 when the AHI index is slightly abnormal, by 2 when the AHI index is moderately abnormal, or by 3 when the AHI index is severely abnormal;
Step 3: producing sound, light and vibration alarms, wherein an alarm device is driven to produce at least one of the sound, light and vibration alarms to remind a user or a guardian of the user, and provide a corresponding early warning level, wherein a higher early warning level indicates a higher risk of sudden death, the early warning level greater than 3 indicates a necessity of medical attention, and the early warning level greater than 5 indicates a necessity of emergency medical attention;
Step 4: generating an alarming log or a monitoring log, wherein when the result of the abnormality detection in Step 2 indicates normal, the monitoring log is generated, or when the result of the abnormality detection in Step 2 indicates abnormal, the alarming log is recorded and generated after the alarms are produced in Step 3;
Step 5: transmitting data through network, wherein the obtained original physiological signals, the generated alarming log, and the generated monitoring log are transmitted to a network server terminal for data analysis processing and storage backup; and
Step 6: feeding back expert diagnosis and treatment information, wherein abnormal data obtained by monitoring are pushed by the network server to a medical care terminal, where a medical expert makes an early warning assessment on a risk of sudden death, and formulates and feeds back corresponding diagnosis and treatment guidance to the user or the guardian of the user through network;
wherein the information about respiration reflects a working status of a respiratory system, and the respiratory rate and an apnea hypopnea index AHI during sleep are monitored respectively,
wherein the detecting of the respiratory rate is described with an equation (1):

$$RESP = \frac{60}{T_{RESP}} \qquad (1)$$

where $T_{RESP}$ denotes a respiratory interval in a detected respiratory wave; and
wherein the apnea hypopnea index AHI denotes a number of times of apnea plus hypopnea per hour of sleep; and
wherein the Poincaré map indicators SD1 and SD2 reflect both a working status of a cardiovascular system and a working status of a nervous system;
wherein the heart rate variability is extracted and detected by a non-linear analysis method of heart rate variability, and the standard deviations SD1 and SD2 of Poincaré map in a heart rate interval are calculated, as described in equations (6) and (7):

$$SD1^2 = \frac{1}{N-1}\sum_{i=1}^{N-1}(D'_i)^2, \qquad (6)$$

$$SD2^2 = \frac{1}{N-1}\sum_{i=1}^{N-1}(D''_i)^2, \qquad (7)$$

where $D'_i$ and $D''_i$ are described in equations (8) and (9), and N denotes a total number of heart rate intervals:

$$D'_i = \frac{1}{\sqrt{2}}|TRR_n - TRR_{n+1}|, \qquad (8)$$

$$D'_i = \frac{1}{\sqrt{2}}|TRR_n + TRR_{n+1} - 2\overline{TRR}|, \qquad (9)$$

where $TRR_n$ and $TRR_{n+1}$ denote respectively an $n^{th}$ heart rate and a $(n+1)^{th}$ heart rate interval, $\overline{TRR}$ denotes an interval mean value of all heart rate intervals, and n is a natural number; and the Poincaré map indicators SD1 and SD2 are normal when an empirical value of SD1 is greater than or equal to 10 ms and an empirical value of SD2 is greater than or equal to 20 ms, and the Poincare map indicators SD1 and SD2 are abnormal when an empirical value of SD1 is smaller than 10 ms or an empirical value of SD2 is smaller than 20 ms.

2. The early warning method of sudden death according to claim 1, wherein the information about arterial blood oxygen saturation reflects both a working status of a respiratory system and a working status of a cardiovascular system;

the arterial oxygen saturation is detected by a dual-wavelength photoplethysmographic sensor with red light at a wavelength of 660 nm and infrared light at a wavelength of 940 nm, and is described with equations (2) and (4), or (3) and (4):

$$S_pO_2 = \alpha - \beta R \qquad (2)$$

$$S_pO_2 = \alpha - \beta R - \gamma R^2 \qquad (3)$$

$$R = \frac{I_{AC}^{660}/I_{DC}^{660}}{I_{AC}^{940}/I_{DC}^{940}}, \qquad (4)$$

where $I_{AC}^{660}$ and $I_{AC}^{940}$ denote respectively an AC component of an intensity of the red light and an AC component of an intensity of the infrared light, $I_{AC}^{660}$ and $I_{AC}^{940}$ denote respectively a DC component of the intensity of the red light and a DC component of the intensity of the infrared light, and α, β and γ each denote an empirical value;

wherein the equation (2) denotes a first-order linear relation between the blood oxygen saturation and a R value, and the second-order equation (3) is used when the first-order relation is not linear.

3. The early warning method of sudden death according to claim 1, wherein the information about heart rate reflects a working status of a cardiovascular system, wherein the heart rate is detected and described with an equation (5):

$$HR = \frac{60}{T_{RR}}, \qquad (5)$$

where $T_{RR}$ denotes a heart rate interval in a body surface electrocardiogram or a photoplethysmographic.

4. The early warning method of sudden death according to claim 1, wherein in Step 2, a normal respiratory rate ranges from 10 times/min to 24 times/min, and an respiratory rate greater than 24 times/min or smaller than 10 times/min is abnormal;

wherein AHI smaller than or equal to 5 is normal, AHI greater than 5 and smaller than or equal to 15 is slightly abnormal, AHI greater than 15 and smaller than or equal to 30 is moderately abnormal, and AHI greater than 30 is severely abnormal;

wherein the arterial oxygen saturation greater than or equal to 90% is normal, and the arterial oxygen saturation smaller than 90% is abnormal;

wherein the heart rate in a range of 60 times/min to 100 times/min is normal, and the heart rate greater than 100 times/min or smaller than 60 times/min is abnormal; and wherein the Poincare map indicators SD1 and SD2 are normal when an empirical value of SD1 is greater than or equal to 10 ms and an empirical value of SD2 is greater than or equal to 20 ms, and the Poincare map indicators SD1 and SD2 are abnormal when an empirical value of SD1 is smaller than 10 ms or an empirical value of SD2 is smaller than 20 ms.

\* \* \* \* \*